(12) United States Patent
Saccardo et al.

(10) Patent No.: US 6,491,630 B1
(45) Date of Patent: Dec. 10, 2002

(54) ULTRASOUND IMAGING DEVICE HAVING A SOFT KEYBOARD FOR ENTERING DATA

(75) Inventors: Grace M Saccardo, Bolton, MA (US); Rachel M. Kinicki, Acton, MA (US); Donald W. Lewallen, Andover, MA (US); Daniel Gerard Maier, Methuen, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 59 days.

(21) Appl. No.: 09/710,984

(22) Filed: Nov. 9, 2000

(51) Int. Cl.[7] .................................................. A61B 8/00
(52) U.S. Cl. ...................................................... 600/437
(58) Field of Search ................................. 600/437, 443, 600/447; 382/128

(56) References Cited

U.S. PATENT DOCUMENTS

| | | |
|---|---|---|
| 5,590,658 A | 1/1997 | Chiang et al. |
| 5,603,323 A | 2/1997 | Pflugrath et al. |
| 5,636,631 A | 6/1997 | Waitz et al. |
| 5,690,114 A | 11/1997 | Chiang et al. |
| 5,715,823 A | 2/1998 | Wood et al. |
| 5,722,412 A | 3/1998 | Pflugrath et al. |
| 5,734,915 A * | 3/1998 | Roewer ...................... 395/773 |
| 5,801,941 A * | 9/1998 | Bertram ...................... 364/188 |
| 5,817,024 A | 10/1998 | Ogle et al. |
| 5,839,442 A | 11/1998 | Chiang et al. |
| 5,851,186 A | 12/1998 | Wood et al. |
| 5,879,303 A | 3/1999 | Averkiou et al. |
| 5,891,035 A | 4/1999 | Wood et al. |
| 5,893,363 A | 4/1999 | Little et al. |
| 5,897,498 A | 4/1999 | Canfield et al. |
| 5,938,607 A | 8/1999 | Jago et al. |
| 5,957,846 A | 9/1999 | Chiang et al. |
| 5,964,709 A | 10/1999 | Chiang et al. |
| 5,997,479 A | 12/1999 | Savord et al. |
| 6,007,490 A | 12/1999 | Pawluskiewicz |
| 6,013,032 A | 1/2000 | Savord |
| 6,063,030 A * | 5/2000 | Vara et al. |
| 6,102,863 A | 8/2000 | Pflugrath et al. |
| 6,106,468 A | 8/2000 | Dowdell |
| 6,106,472 A | 8/2000 | Chiang et al. |
| 6,113,547 A | 9/2000 | Catallo et al. |
| 6,117,084 A | 9/2000 | Green et al. |
| 6,117,085 A | 9/2000 | Picatti et al. |
| 6,135,961 A | 10/2000 | Pflugrath et al. |

* cited by examiner

*Primary Examiner*—Francis J. Jaworski
(74) *Attorney, Agent, or Firm*—John Vodopia

(57) ABSTRACT

An ultrasound imaging device including a display which displays an ultrasound image of an object (such as a portion of a body of a patient) and a soft keyboard displayed on the display, which enables entering of identification information relating to the ultrasound image. The soft keyboard replaces the ultrasound image during an identification entry mode, to easily enable the entry of the identification information. The identification information may be patient identification information or date/time information, for example. The ultrasound imaging device may include software which enables the soft keyboard to be displayed in a plurality of different languages.

32 Claims, 7 Drawing Sheets

ULTRASOUND IMAGING DEVICE HAVING A SOFT KEYBOARD FOR ENTERING DATA

BACKGROUND OF THE INVENTION

1. Field of the Invention

The present invention relates to an ultrasound imaging device which enables simple and easy entry of information relating to an ultrasound image, and more particularly, to an ultrasound imaging device having a soft keyboard displayed on a screen of the ultrasound imaging device which is used to enter the information.

2. Description of the Related Art

In the past, ultrasound imaging devices have implemented an alphanumeric keyboard as part of a control panel to enable a user to enter patient identification information. Through the alphanumeric keyboard, the patient's name and/or other patient identification data can be displayed and stored along with an ultrasound image of the patient. The complexity and size of the control panel are increased due to the implementation of the alphanumeric keyboard, and the alphanumeric keyboard has additional keys which are irrelevant with regard to entering the patient identification information. On such a control panel, the size and spacing of the alphanumeric keys are usually smaller than that of a standard keyboard, making use of the control panel alphanumeric keyboard less than optimal. The additional space required for the alphanumeric keyboard may result in a more intimidating user interface, particularly for someone who does not perform diagnostic ultrasound imaging functions as a primary part of their occupation, such as someone other than a full-time diagnostic ultrasound sonographer. The additional space also results in a larger overall ultrasound imaging device.

Because the control panel alphanumeric keyboard is of a fixed configuration, it is not possible to easily convert the use of the alphanumeric keyboard to be compatible with a plurality of different languages. Accordingly, manufacturing inventory and selling costs are increased as a result of localization requirements of the alphanumeric keyboard on the control panel for the various different languages.

SUMMARY OF THE INVENTION

Various objects and advantages of the invention will be set forth in part in the description which follows and, in part, will be obvious from the description, or may be learned by practice of the invention.

The present invention is achieved by providing an ultrasound imaging device comprising a display which displays an ultrasound image of an object, and a soft keyboard displayed on the display, which enables entering of identification information such as information relating to the ultrasound image.

The present invention is also achieved by providing a portable ultrasound imaging device comprising a display which displays an ultrasound image of a portion of a body of a patient, a patient identification input key which enables the ultrasound imaging device to enter a patient identification entry mode, and a soft keyboard which replaces the ultrasound image on the display in response to activation of the patient identification input key, to enable identification of the ultrasound image.

BRIEF DESCRIPTION OF THE DRAWINGS

The various objects and advantages of the invention will become apparent and more readily appreciated from the following description of the preferred embodiments, taken in conjunction with the accompanying drawings of which.

DESCRIPTION OF THE PREFERRED EMBODIMENTS

Figure 1:
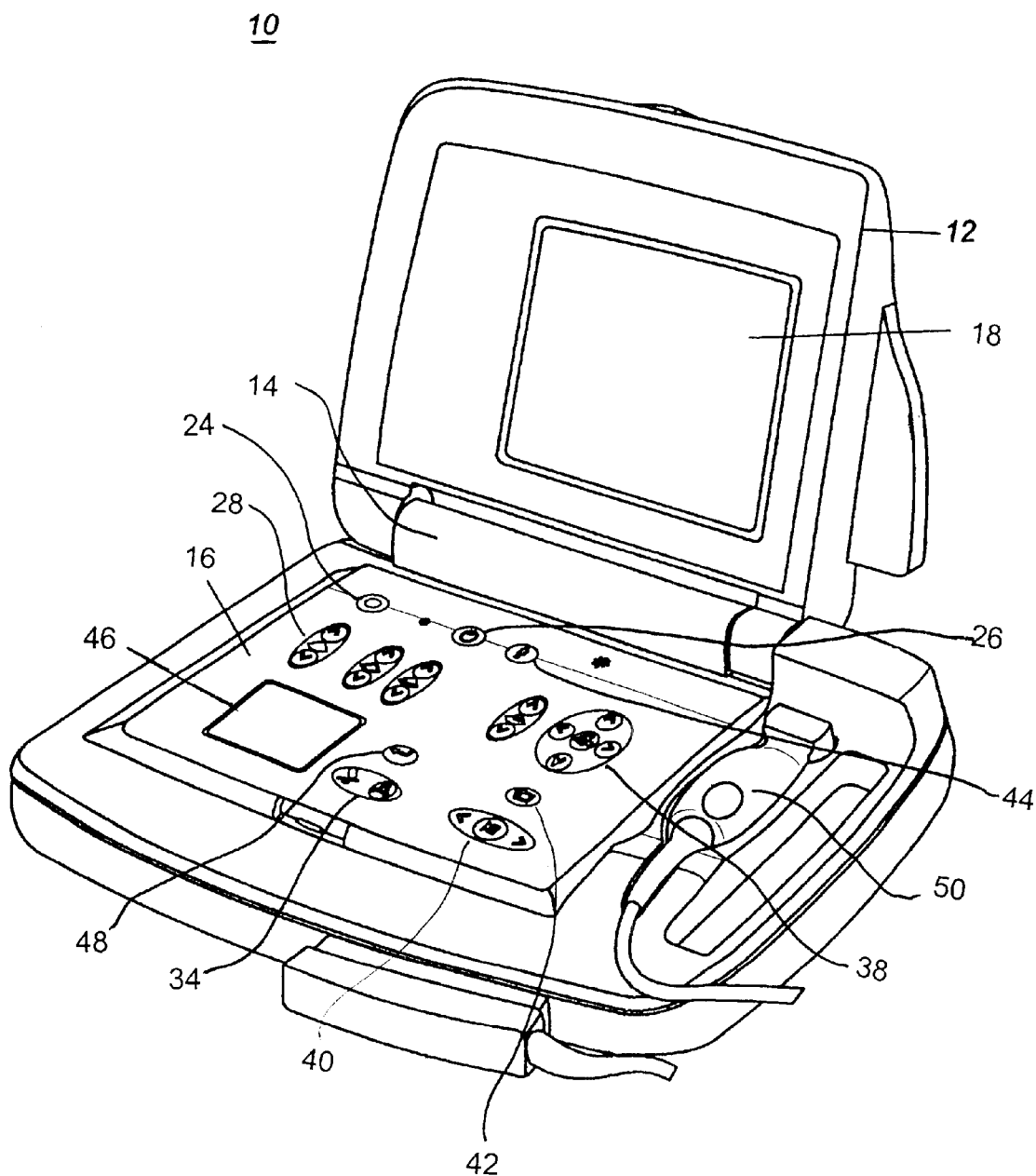
FIG. 1 is a birds-eye view of an ultrasound imaging device according to an embodiment of the invention.

Reference will now be made in detail to the present preferred embodiments of the present invention, examples of which are illustrated in the accompanying drawings, wherein like reference numerals refer to the like elements throughout.

FIG. 1 is a birds-eye view of an ultrasound imaging device 10 in accordance with an embodiment of the present invention. The ultrasound imaging device 10 is a small portable ultrasound system intended for personal use, such as by a doctor. The ultrasound imaging device 10 may be somewhat like a laptop device, so that it may be taken on doctors rounds in a hospital. It may also be in a doctor's office where the doctor would want to perform a quick check of a particular interior portion of a patient's body. A cardiologist may use such a device to make sure the heart looks healthy, instead of just listening to the heartbeat. Of course, the ultrasound imaging device 10 can be stationary, without the ability to be easily transportable. The user interface of the ultrasound imaging device 10 provides those controls which are used for generating a diagnostic quality ultrasound image and to tag the ultrasound image with the patient ID and date and time information.

The ultrasound imaging device 10 has a top panel 12 which swivels relative to a bottom panel 16 about a hinge assembly 14. The top panel 12 includes a display 18 for displaying an ultrasound image. The bottom panel 16 includes controls for entering patient identification and date and time information relating to the ultrasound image and for storing the ultrasound image along with the patient identification information and date and time information.

Figure 2:
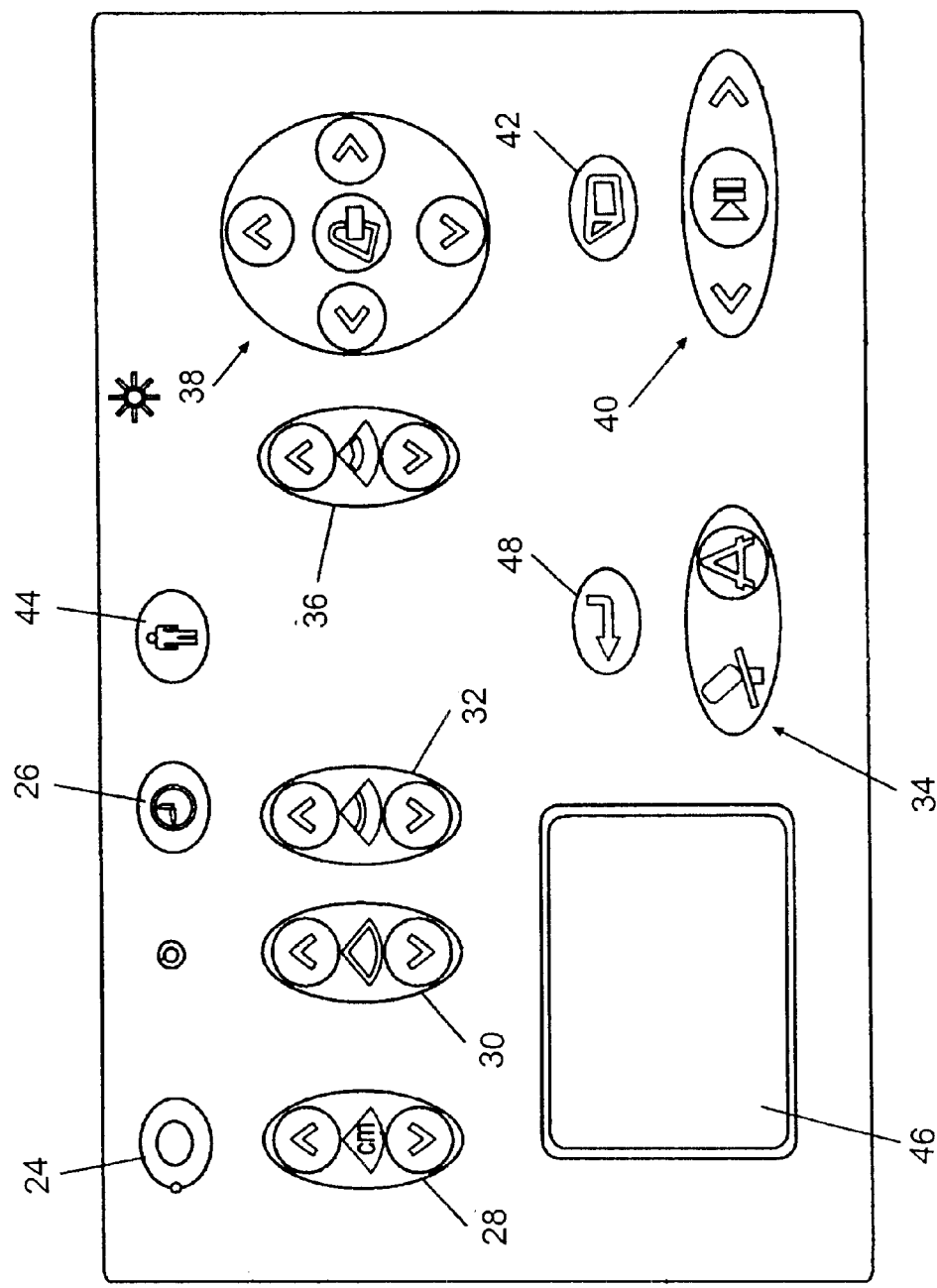
FIG. 2 is a close-up view of control keys for controlling various aspects of the display of the ultrasound imaging device shown in FIG. 1.

FIG. 2 shows a close-up view of control keys for controlling operation of the ultrasound imaging device 10. The power ON/OFF key 24 turns the ultrasound imaging device ON/OFF, a date/time entry key 26 enables entry and updating of the current date and time, a depth key 28 adjusts the depth of an ultrasound image, a 2D overall gain key 30 and a 2D near field gain key 32 adjust the 2D overall gain and 2D near field gain of the ultrasound image, and element 34 is a caliper and erase key. A color gain key 36 enables adjustment of color gain of the ultrasound image and a color ON/OFF and wedge positioning key 38 enables adjustment of these features of the ultrasound image. A freeze and image review key 40 freezes the real-time display of ultrasound images and enables image review of previously acquired ultrasound images. A store image key 42 enables the storage of the current ultrasound image being displayed to a flash card (memory 70 shown in FIG. 7).

A patient ID entry mode key 44 enables a user of the ultrasound imaging device 10 to enter and exit the patient ID entry mode, wherein such a mode is used to enter patient identification information corresponding to a currently displayed ultrasound image. The operations of a touch-pad 46 and a select key 48 are used to enter the patient identification information during the patient ID entry mode and further details of the operations of these elements will be described later.

Figure 3:
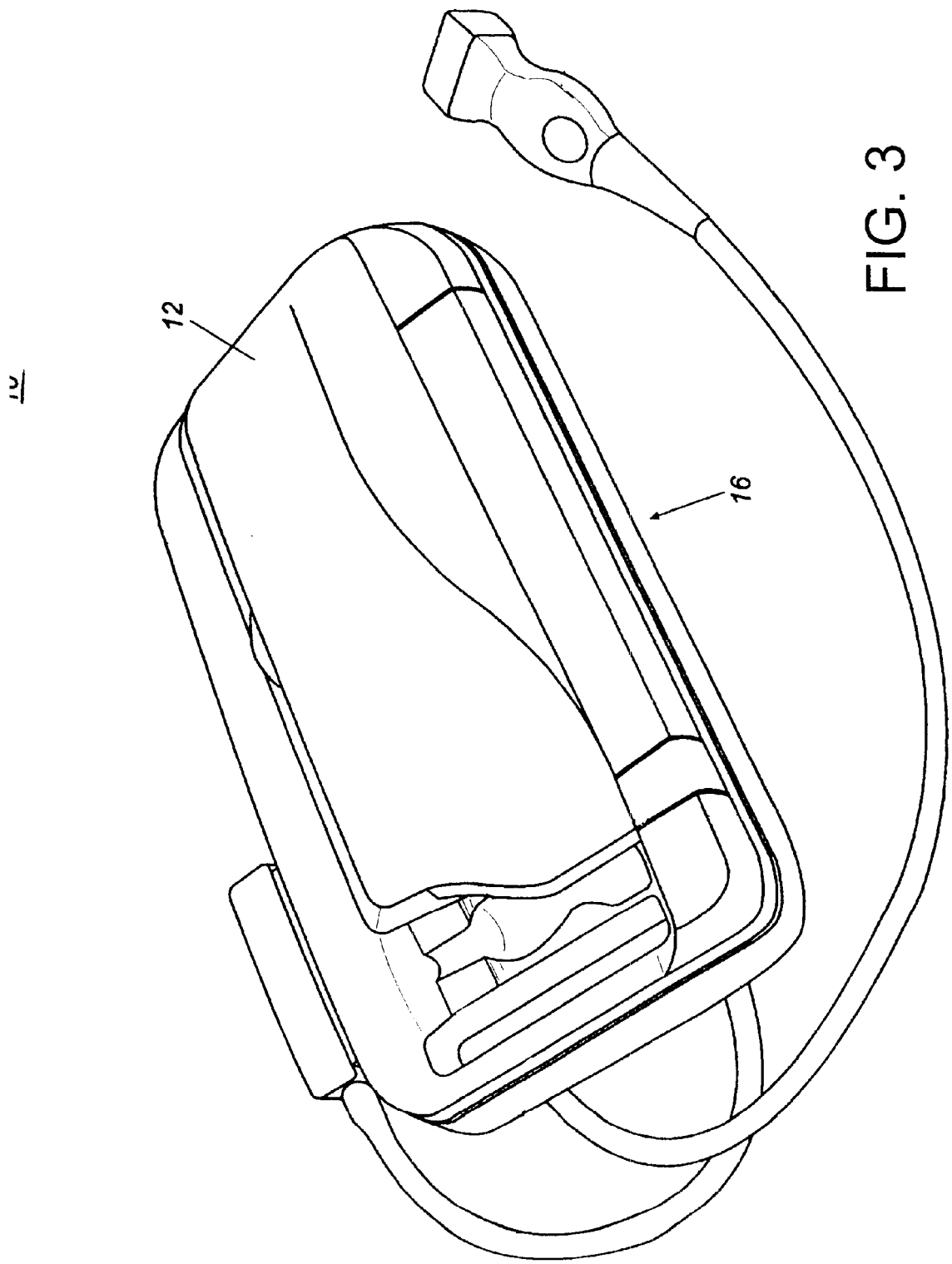
FIG. 3 is a top view of the ultrasound imaging device shown in FIG. 1, with a hinged display being in a closed position.

FIG. 3 is a top view of the ultrasound imaging device 10 with the top panel 12 in a closed position, rotated to contact the bottom panel 16 and cover the various control keys formed in the bottom panel 16.

Figure 4:
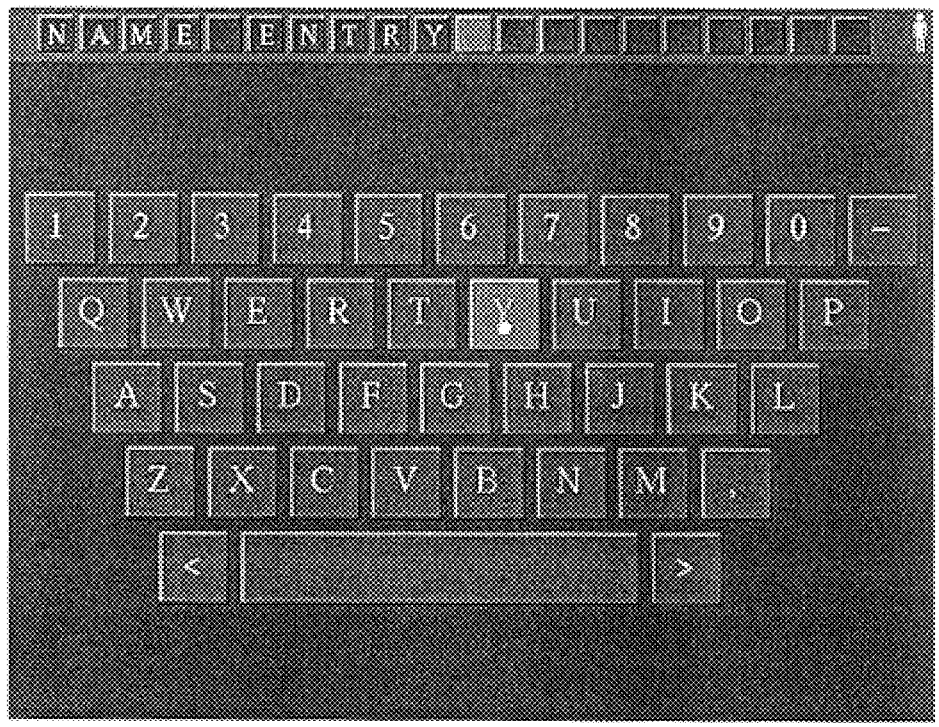
FIG. 4 is a plan view of a soft keyboard in English shown on the display of the ultrasound imaging device shown in FIG. 1 during a patient identification (ID) information entry mode.

FIG. 4 shows a soft keyboard 60 which is displayed on the display 18 in the patient ID entry mode. The ultrasound imaging device 10 utilizes software to implement the software keyboard as part of the patient identification feature. The user-entered patient identification information may comprise alphabetic characters, numbers, certain symbols, and space characters. The characters are presented to the user in a picture of a soft keyboard (virtual keyboard) that appears on the display 18. The display 18 may be a liquid crystal display (LCD).

A user enters the patient ID entry mode by pressing the patient ID entry mode key 44. The display 18 then displays the soft keyboard 60. As shown in FIG. 4, the characters presented on the soft keyboard 60 are capitalized and localized for English, but the characters need not be capitalized nor localized for English. The patient ID entry mode may be exited by pressing the patient ID entry mode key 44 again or any control key other than the touch-pad 46 or the select key 48. Once the patient ID entry mode is exited, the ultrasound imaging device 10 returns to displaying its prior imaging state on the display 18.

Once the ultrasound imaging device 10 enters the patient ID entry mode, the user uses the touch-pad 46 to scroll over the soft keyboard 60 to a desired character to be input. Touch-pad motion is reflected in movement around the soft keyboard 60. As the touch-pad motion is detected, the current active character changes accordingly. The current active character is highlighted. Pressing the select key 48 while a particular character is highlighted causes the currently highlighted character on the keyboard to be input into the patient identification information and displayed on the display 18. Additional characters may be selected in the same manner. As the next key is highlighted, the previous key is unhighlighted, so that it is apparent which key is to be selected when the select key 48 is pressed. Selecting the "<" and ">" keys on the soft keyboard 60 allows the user to traverse backward and forward respectively within the patient identification information to edit different characters.

Instead of using the touch-pad 46, it is readily contemplated that another type of control to enter the symbols (characters, numbers, etc.) of the patient identification information using the soft keyboard 60 may be used. For example, the soft keyboard 60 may be a touch soft keyboard in which the symbols are entered based upon the location of the touch of a finger of the user on the display 18. A mouse or tracking ball may also be used to highlight and select the various characters, numbers, etc. of the keys of the soft keyboard 60. Any other type of system and method to highlight and/or select the various keys of the soft keyboard may be used to enter the patient identification information in the patient ID entry mode.

If patient identification information has been entered, the patient identification information is displayed in live and frozen imaging modes of ultrasound images. In this particular embodiment, the patient identification information is not stored in non-volatile (battery backed up) memory, and thus blank patient identification is displayed when the system is initially powered on. Further, the current patient identification is "erased" when the patient ID entry mode is newly entered. However, it is contemplated that the patient identification information may be stored in memory when the ultrasound imaging device is turned off and that the current patient identification is not "erased" when the patient ID entry mode is re-entered.

The software keyboard may be programmed so that a plurality of languages and keyboard configurations are stored in the ultrasound imaging device 10. If German or French language entry (just two examples of possible languages) of patient identification information is desired, the software keyboard can be easily changed to show the appropriate characters and/or symbols of the desired language.

Figure 5:
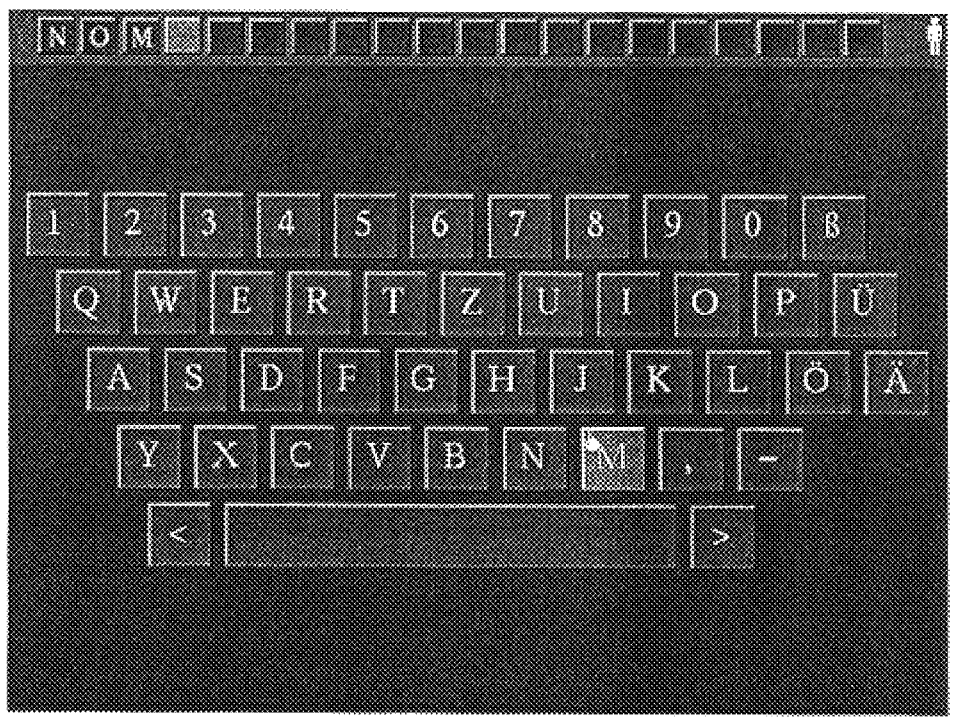
FIG. 5 is a plan view of a soft keyboard in German shown on the display of the ultrasound imaging device shown in FIG. 1 during the patient identification information entry mode.

The soft keyboard 60 shown in FIG. 4 has fewer keys than a standard physical keyboard and is in English. The soft keyboard 60 has keys for each of the letters of the English alphabet, the numbers 0–9, the "–", "<",">", "," and space bar. The other keys of a standard physical keyboard are not necessary to enter the patient identification information, thereby simplifying the soft keyboard 60 and minimizing the opportunity for misstroking keys. A soft keyboard 62 in German as shown in FIG. 5 is displayed on the display 18 if the German language soft keyboard is selected by a user.

Figure 6:
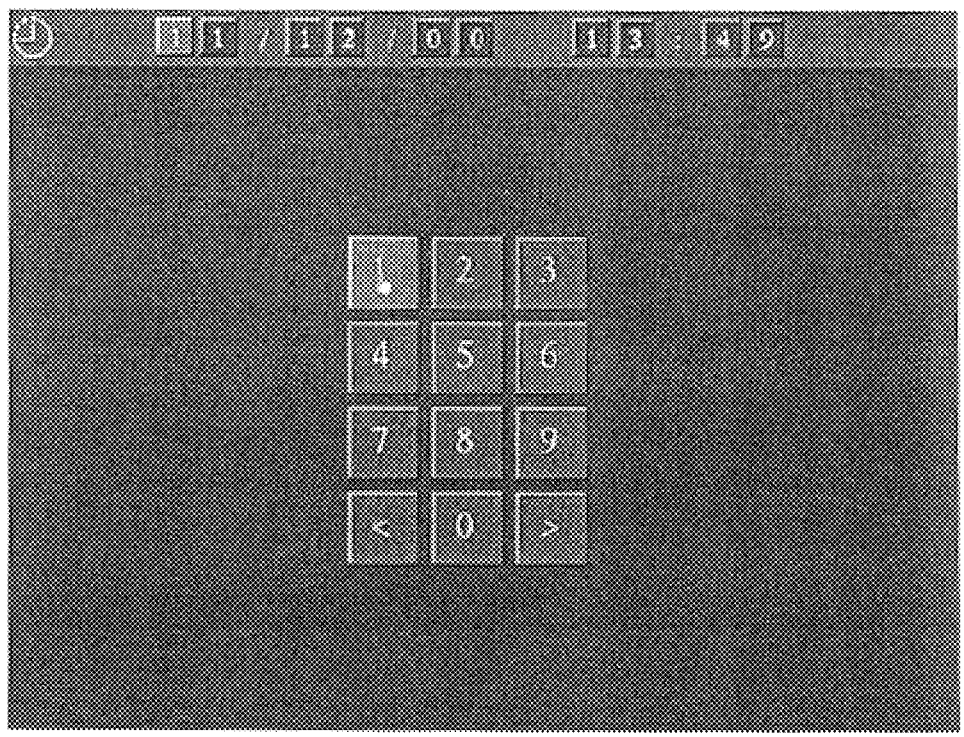
FIG. 6 is a plan view of a soft keyboard shown on the display of the ultrasound imaging device shown in FIG. 1 during a date/time entry mode.

The soft keyboard is also usable for setting the system date and time. When the date/time entry key 26 is pressed, the ultrasound imaging device 10 enters a date/time entry mode as shown in FIG. 6. The keys of a soft keyboard 63 may be highlighted and selected as noted above. The set system date and time are stored in non-volatile memory and are updated appropriately even when the ultrasound imaging device 10 is turned off.

Figure 7:
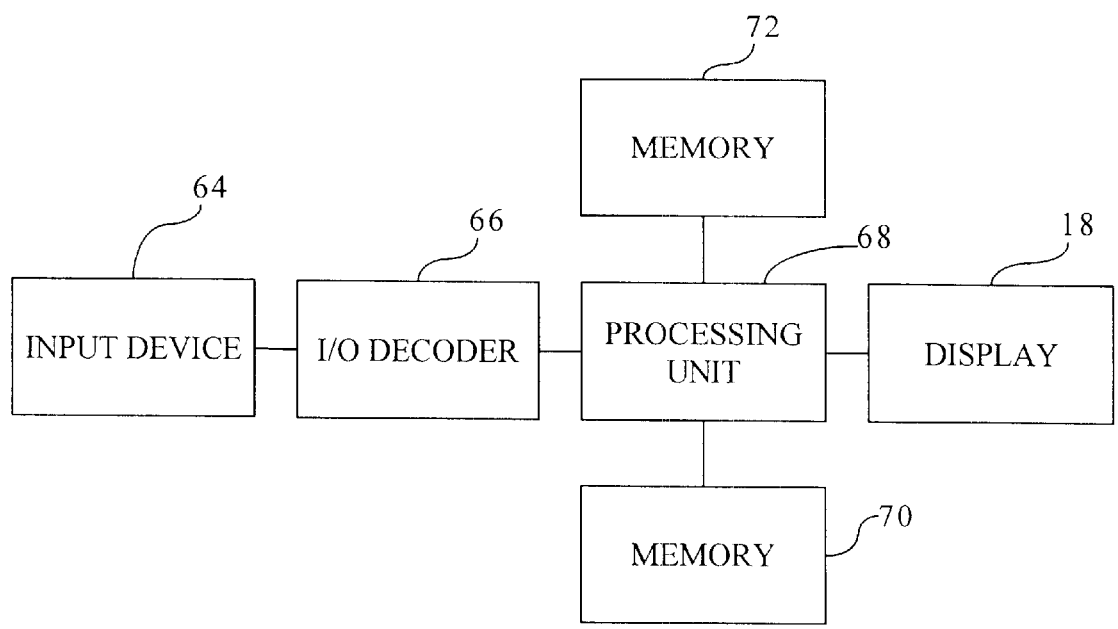
FIG. 7 is a block diagram of the system for entering patient identification information into the ultrasound imaging device through the use of the soft keyboard.

FIG. 7 shows a block diagram of the system for entering patient identification information and date/time information into the ultrasound imaging device 10. Other modes and/or types of information may be entered as identification information as well. The user selects the patient ID entry mode key 44 (or date/time entry key 26) from the control panel (which forms part of the input device 64). An input/output decoder 66 detects the key selection and decides which key was selected. The input/output decoder 66 (formed for example by an ASIC) sends a message to a processing unit 68 (comprising for example a microprocessor and associated memory) which activates the appropriate software module to handle the key selection and display the appropriate soft keyboard on the display 18. The input/output decoder 66 also detects touch pad motion and the select key. As the software program for the soft keyboard 60 is being executed in a processing unit 68, the user highlights various keys of the soft keyboard 60 and enters the patient identification information using the touch-pad 46 and the select key 48 (which also form a part of the input device 64). Each input is passed to the system software which processes it and updates the display 18 appropriately (new letter selected, new soft key to highlight on the soft keyboard, etc.). When the entry mode is exited, the input/output decoder 66 sends another message to the system software which erases the soft keyboard and re-displays the ultrasound image with the newly entered date/time and/or patient identification information. A patient identification icon is always displayed with the image so that the user can easily locate the patient ID information on the display. If the user wants to store this image, the user selects the storage image key 42 from the control panel and the video image on the display (the video image include everything displayed on the display so the video display includes the ultrasound image, patient ID, date/time, etc., if entered) is written to a removable memory device (such as a flash RAM memory (flash card) or any other type of suitable memory) 70. It is not stored automatically. Details relating to the removable memory device 70 is the subject of a co-pending application, Ser. No. 09/710,593 commonly assigned to the assignee of this application.

The removable memory device 70 can then be taken out and put in a computer to be readjust like the flashcards in digital cameras.

A non-volatile memory 72 is where the date/time information is stored.

When the user wishes to localize the soft keyboard 60 (in other words, switch the language of the soft keyboard 60), the user selects from one of a group of languages stored in the system software. Then the language appropriate keyboard is available for use. Then, the Processing unit 68 executes the system software for the newly selected language. Subsequently, the new soft keyboard 62 in the new language is displayed on the display 18, and is ready to receive input in the new language from the touch-pad 46 and the select key 48 (which form part of the input device 64). Details relating to the multiple language keyboards is the subject of a co-pending application, Ser. No. 09/710,609 commonly assigned to the assignee of this application.

As noted previously, the software keyboard allows the user to enter patient identification information without complicating the control panel with additional keys. For those users who do not typically enter patient identification information, the control panel is simpler and uncluttered with unnecessary keys. Adding new local languages becomes a simple software change, rather than one involving designing and manufacturing a new keyboard. Additionally, even if a user wants to annotate an ultrasound image with patient identification information, the ultrasound imaging device does not require any extra physical space for a physical keyboard having hard keys. Further, if the user never annotates his/her ultrasound images, the user is never bothered with a physical keyboard, as the soft keys of the soft keyboard are hidden from view when the ultrasound imaging device is not in the patient ID entry mode, as noted previously.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An ultrasound imaging device comprising:
    means for obtaining an ultrasound image of an object;
    a display configured for displaying the ultrasound image of the object;
    a processor storing a plurality of soft keyboards and configured for receiving commands for displaying at least one of the plurality of soft keyboards on the display, wherein at least one of the soft keyboards enables entering of identification information relating to the ultrasound image; and
    means for selecting a soft keyboard belonging to a particular group of soft keyboards of the plurality of soft keyboards and for programming the processor for displaying the selected soft keyboard on the display when a soft keyboard from the particular group of soft keyboards needs to be displayed.

2. The ultrasound imaging device as claimed in claim 1, wherein the identification information is patient identification information indicating the patient's name and/or ID and/or a portion of a body of a patient which is the object.

3. The ultrasound imaging device as claimed in claim 2, further comprising:
    a touch-pad which selectively highlights keys of the soft keyboard based upon user manipulation; and
    a select key which selects the highlighted key of the soft keyboard, to enter the patient identification information.

4. The ultrasound imaging device as claimed in claim 2, further comprising:
    a mouse, track ball or touch display which selects keys of the soft keyboard based upon user manipulation, to enter the patient identification information.

5. The ultrasound imaging device as claimed in claim 2, further comprising software which selectively displays the soft keyboard on the display in a plurality of languages, based upon a user input.

6. The ultrasound imaging device as claimed in claim 2, further comprising:
    an identification input key which enables the ultrasound imaging device to enter an identification entry mode for entering the patient identification information, wherein the display displays the soft keyboard in response to activation by the identification input key;
    wherein the display deletes any of the identification information already entered in response to the ultrasound imaging device being turned off or in response to the identification input key being activated.

7. The ultrasound imaging device as claimed in claim 2, further comprising:
    a storage device which stores the ultrasound image and corresponding patient identification information.

8. The ultrasound imaging device as claimed in claim 7, wherein the storage device is a flash RAM memory.

9. The ultrasound imaging device as claimed in claim 2, further comprising:
    an input/output decoder which receives key inputs by the user; and
    a Processing unit which receives the key inputs from the input/output decoder and executes the program to display the soft keyboard on the display and process the patient identification information input by the user through the soft keyboard.

10. The ultrasound imaging device as claimed in claim 2, wherein the soft keyboard consists of only the 26 letters of the English alphabet, the 10 roman numerals, a hyphen key, a comma key, back and forward arrow keys, and a space bar.

11. The ultrasound imaging device as claimed in claim 2, further comprising
    an identification input key which enables the ultrasound imaging device to enter a patient identification entry mode for entering the patient identification information, wherein the display displays the soft keyboard in response to activation by the patient identification input key;

a touch-pad which selectively highlights keys of the soft keyboard based upon user manipulation;

a select key which selects the highlighted key of the soft keyboard, to enter the identification information; and a plurality of control keys which control the display of the ultrasound image, wherein the ultrasound imaging device exits the patient identification input entry mode upon activation of one of the control keys or reactivation of the identification input key.

12. The ultrasound imaging device as claimed in claim 1, further comprising:

an identification input key which enables the ultrasound imaging device to enter an identification entry mode for entering the information, wherein the display displays the soft keyboard in response to activation of the identification input key.

13. The ultrasound imaging device as claimed in claim 12, further comprising:

a touch-pad which selectively highlights keys of the soft keyboard based upon user manipulation; and a select key which selects the highlighted key of the soft keyboard, to enter the identification information.

14. The ultrasound imaging device as claimed in claim 2, further comprising:

a mouse, track ball or touch display which selects keys of the soft keyboard based upon user manipulation, to enter the information.

15. The ultrasound imaging device as claimed in claim 12, further comprising:

an input/output decoder which receives key inputs by the user; and a Processing unit which receives the key inputs from the input/output decoder and executes the program to display the soft keyboard on the display and process the information input by the user through the soft keyboard, in response to the ultrasound imaging device entering the identification entry mode.

16. The ultrasound imaging device as claimed in claim 12, wherein the soft keyboard consists of only the 10 roman numerals, and back and forward arrow keys.

17. The ultrasound imaging device as claimed in claim 1, further comprising software which selectively displays the soft keyboard on the display in a plurality of languages, based upon a user input.

18. The ultrasound imaging device as claimed in claim 17, further comprising:

a processing element which selectively displays the soft keyboard on the display in the plurality of languages, processes the identification information input by a user through the soft keyboard, in response to the ultrasound imaging device entering the identification entry mode and another user input indicating one of the plurality of languages for display of the soft keyboard.

19. The ultrasound imaging device as claimed in claim 1, further comprising:

a storage device which stores the ultrasound image and corresponding information.

20. The ultrasound imaging device as claimed in claim 19, wherein the storage device is a flash RAM memory.

21. The ultrasound imaging device as claimed in claim 1, wherein the identification information is date/time information.

22. The ultrasound imaging device as claimed in claim 21, further comprising:

a touch-pad which selectively highlights keys of the soft keyboard based upon user manipulation; and a select key which selects the highlighted key of the soft keyboard, to enter the date/time information.

23. The ultrasound imaging device as claimed in claim 21, further comprising:

a mouse, track ball or touch display which selects keys of the soft keyboard based upon user manipulation, to enter the date/time information.

24. The ultrasound imaging device as claimed in claim 21, further comprising:

a date/time entry mode key which enables the ultrasound imaging device to enter an date/time entry mode for entering the date/time information, wherein the display displays the soft keyboard for entering the date/time information in response to activation of the date/time information entry mode key;

a touch-pad which selectively highlights keys of the soft keyboard based upon user manipulation;

a select key which selects the highlighted key of the soft keyboard, to enter the date/time information; and a plurality of control keys which control the display of the ultrasound image, wherein the ultrasound imaging device exits the date/time entry mode upon activation of one of the control keys or upon reactivation of the date/time entry mode key.

25. The ultrasound imaging device as claimed in claim 1, further comprising:

a date/time entry mode key which enables the ultrasound imaging device to enter an date/time entry mode for entering date/time information, wherein the display displays the soft keyboard for entering the date/time information in response to activation of the date/time information entry mode key.

26. The ultrasound imaging device as claimed in claim 25, further comprising:

a touch-pad which selectively highlights keys of the soft keyboard based upon user manipulation; and a select key which selects the highlighted key of the soft keyboard, to enter the date/time information.

27. The ultrasound imaging device as claimed in claim 25, further comprising:

a mouse, track ball or touch display which selects keys of the soft keyboard based upon user manipulation, to enter the date/time information.

28. A portable ultrasound imaging device comprising:

a display which displays an ultrasound image of a portion of a body of a patient;

a patient identification input key which enables the ultrasound imaging device to enter a patient identification entry mode;

a soft keyboard which replaces the ultrasound image on the display in response to activation of the patient identification input key, to enable identification of the ultrasound image; and means for selecting another soft keyboard to replace the soft keyboard displayed by the display, wherein the two soft keyboards correspond to a particular group of soft keyboards.

29. The portable ultrasound imaging device as claimed in claim 28, further comprising:

a bottom panel having control keys to control features of the ultrasound image on the display; and a top panel connected to and rotatable relative to the bottom panel, wherein the top panel has the display.

30. The portable ultrasound imaging device as claimed in claim 29, wherein the top panel folds over the bottom panel to a closed position to protect the display and the control keys from external elements.

31. The portable ultrasound imaging device as claimed in claim 28, wherein the particular group of soft keyboards includes soft keyboards corresponding to a plurality of languages.

32. The ultrasound imaging device as claimed in claim 1, wherein the particular group of soft keyboards includes soft keyboards corresponding to a plurality of languages.

* * * * *